United States Patent [19]

Arnold

[11] Patent Number: 4,599,200

[45] Date of Patent: Jul. 8, 1986

[54] PROCESS FOR THE PRODUCTION OF 17α-ACETOXY-1α,2α-METHYLENE-4,6-PREGNADIENE-3,20-DIONE

[75] Inventor: Hanfried Arnold, Berlin, Fed. Rep. of Germany

[73] Assignee: Schering Aktiengesellschaft, Berlin and Bergkamen, Fed. Rep. of Germany

[21] Appl. No.: 648,202

[22] Filed: Sep. 7, 1984

[30] Foreign Application Priority Data

Sep. 7, 1983 [DE] Fed. Rep. of Germany ....... 3332590

[51] Int. Cl.$^4$ ............................................. C07J 71/00
[52] U.S. Cl. ........................................ 260/239.55 C
[58] Field of Search ............................ 260/239.55 C

[56] References Cited

U.S. PATENT DOCUMENTS 3,069,417 12/1962 Weiss et al. ................. 260/239.55 C
3,079,382 2/1963 Camerino et al. ......... 260/239.55 C

*Primary Examiner*—Elbert L. Roberts
*Attorney, Agent, or Firm*—Millen & White

[57] ABSTRACT

A multistep process for production of 17α-acetoxy-1,2-methylene-4,6-pregnadiene-3,20-dione involves ketalization of the 20-keto group of 17α-hydroxy-1,4,6-pregnatriene-3,20-dione, then methylenation in the 1,2-position with trimethylsulfoxonium iodide, hydrolysis and simultaneous acetylation of the 17α-hydroxy group.

7 Claims, No Drawings

PROCESS FOR THE PRODUCTION OF 17α-ACETOXY-1α,2α-METHYLENE-4,6-PREGNADIENE-3,20-DIONE

BACKGROUND OF THE INVENTION

The process of this invention relates to the production of 17α-acetoxy-1,2-methylene-4,6-pregnadiene-3,20-dione which can be used conventionally in the synthesis of the known steroid hormone cyproterone acetate (6-chloro-17α-acetoxy-1,2-methylene-4,6-pregnadiene-3,20-dione).

According to the known synthesis, $\Delta$1,6-hydroxyprogestrone is reacted with dimethylsulfoxonium methylide to form the 1α,2α-methylene compound (DE PS 1,183,500). However, this process has the drawback that this methylenation reaction does not progress uniformly, since the methylenation reagent also partly attacks the 20-keto group.

SUMMARY OF THE INVENTION

Accordingly, it is an object of this invention to provide an improved process for the production of 17α-acetoxy-1α,2α-methylene-4,6-pregnadiene-3,20-dione, e.g., which produces better yields.

Upon further study of the specification and appended claims, further objects and advantages of this invention will become apparent to those skilled in the art.

These objects have been achieved by this invention by providing a process wherein the starting material steroid, 17α-hydroxy-1,4,6-pregnatriene-3,20-dione, is ketalized on the 20-keto group with ethylene glycol in the presence of trialkyl formate, preferably trimethyl or triethyl formate, and a strong acid, and then the 20-ketal, by a method known in the art, is methylenated in the 1,2-position with trimethylsulfoxonium iodide in a polar aprotic solvent in the presence of a strong base, and then the resulting 17α-hydroxy-1α,2α-methylene-4,6-pregnadiene-3-keto-20-ethylene ketal is hydrolyzed during work-up to the 20-ketone, and by a method known in the art, is acetylated in the 17α-position with a reactive acetic acid derivative such as acetic anhydride in the presence of an inorganic or organic sulfonic acid.

DETAILED DISCUSSION

Suitable strong acids for ketalization of the 20-keto group include p-toluenesulfonic acid or concentrated sulfuric acid which are particularly suitable. Typical amounts are 0.1-2 mole equivalents in relation to the amount of keto steroid. Equivalent strong acids are well known. Typical, reaction media pH's are less than about 3. Typical reaction temperatures are about 0°-100° C. and reaction times about 30 min. to 12 hours. Typical amounts of ethyl glycol are a slight excess over the stoichiometric and of formates are about 1.1-2.0 mole/mole of steroid.

The next reaction step is per se known. Suitable polar aprotic solvents include dimethyl sulfoxide, dimethylformamide, dimethylacetamide or hexamethylphosphorotriamide. Dimethylformamide is particularly suitable. Actually any (reaction compatible) strong base, such as sodium or potassium hydroxide or sodium hydride, is suitable as a strong base for introduction of the methylene group in the 1,2-position. The amount of trimethylsulfoxonium iodide usually is in a mole ratio of 1:1.1 to 1:4, based on the steroid.

The resultant hydrolysis can be effected with any compatible acid, e.g., sulfuric acid.

The third step is similarly per se known. Actually any (reaction compatible) inorganic or organic sulfonic acid such as sulfuric acid, perchloric acid or p-toluenesulfonic acid is suitable as a strong acid for esterification of the 17α-hydroxy group. The acid is added in an amount of 0.05 to 0.5 mole equivalent in relation to the amount of steroid alcohol. Typical reaction temperatures are about 0°-100 ° C. and times about 30 min. to 6 hours.

The starting material for the first step is known.

The progress of the first reaction step, i.e., ketalization of the 20-keto group of the 17α-hydroxy-1,4,6-pregnatriene-3,20-dione actually was not to be expected since, as is generally known, 3-keto-$\Delta$1,4 systems rearrange themselves under acid conditions into structures with aromatic A rings (cf DE OS No. 29 13 147). As far as 20-ketals are described, the $\Delta^1$ double bond has been introduced (J. Med. Pharm. Chem., 5, (1962) 133), the dienonephenol rearrangement by substitution on the carbon atom C9 and/or C11 or C19 has been prevented (DE OS No. 29 16 889, DE OS No. 29 13 147, U.S. Pat. No. 3,069,417, Helv. Chim. Acta 51, (1968) 1941) or expensive chromatographic purification steps have been used, which suggests strong contamination by byproducts, e.g., by aromatization (U.S. Pat. No. 3,069,417).

Further, it is known that the 20-keto group reacts with greater difficulty when substituents such as halogen or an ester group are in the neighboring position on the carbon atom C21 or C17 (J. Org. Chem., 17, (1952) 1369 and 21 (1956) 65 and also DE AS No. 10 00 812, US PS No. 27 05 720, CA PS No. 542 851).

The process according to this invention is thus a combination of a new inventive step and two process steps known in the art. Although the combination process according to this invention has an additional step, the yield for the end product is ultimately higher (e.g., mole %) than with the known two-step process, in which the 20-keto group is not protected by ketalization before methylenation. Moreover, the process according to the invention has the advantage that methylenation can be performed in dimethylformamide instead of dimethyl sulfoxide, which can be safely recovered and thus does not pollute the environment.

Without further elaboration, it is believed that one skilled in the art can, using the preceding description, utilize the present invention to its fullest extent. The following preferred specific embodiments are, therefore, to be construed as merely illustrative, and not limitative of the remainder of teh disclosure in any way whatsoever. In the following examples, all temperatures are set forth uncorrected in degrees Celsius; unless otherwise indicated, all parts and percentages are by weight.

EXAMPLE (a) 6 g of 17α-hydroxy-1,4,6-pregnatriene-3,20-dione (trienol) are suspended in 30 ml of methylene chloride and, after addition of 3.12 ml of ethylene glycol, 4.5 ml of ethyl orthoformate and 0.6 g of p-toluene sulfonic acid, stirred for 3 hours at room temperature. Neutralization is performed with 0.6 ml of triethylamine, the methylene chloride phase is washed with water and evaporated.

Yield: 6.9 g of trienol-20-ethylene ketal (crude). After recrystallization from methanol: m.p. 205°-207° C.; $[\alpha]_D = -31.3°$ (chloroform); UV: $\epsilon_{220} = 12,040$, $\epsilon_{253} = 9{,}340$, $\epsilon_{298} = 12{,}600$. (This compound has not been described until now.)

(b) 6.61 g of trienol-20-ethylene ketal (crude) are suspended with 6.4 g of trimethylsulfoxonium iodide and 0.93 g of sodium hydroxide pulverized in 66 ml of dimethylformamide and stirred for 4 hours at 50° C. The resulting solution, after addition of 10 ml of 20% sulfuric acid, is stirred for 2 hours at room temperature and then precipitated in water. The crystallizate is washed with water and dried at 80° C.

Yield: 5.42 g of 17α-hydroxy-1,2-methylene-4,6-pregnadiene-3,20-dione, m.p. 232°–237° C., $[\alpha]_D = +169.3°$ (chloroform).

(c) 5.26 g of 17α-hydroxy-1,2-methylene-4,6-pregnadiene-3,20-dione are dissolved in 13 ml of methylene chloride and 7.3 ml of acetic anhydride and, after addition of 0.15 ml of 70% perchloric acid, stirred for 2 hours at 30° C. After addition of 7 ml of water, restirring is performed for 1 hour more at 30° C., the methylene chloride solution is washed with sodium hydrogen carbonate and the methylene chloride is distilled off, after addition of methanol. Teh crystallizate is drawn off, washed with cold methanol and dried at 80° C.

Yield: 4.46 g of 17α-acetoxy-1,2-methyl-4,6-pregnadiene-3,20-dione; melting point 275°–279° C., $[\alpha]_D = +138.6°$ (chloroform).

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of 17α-acetoxy-1,2-methylene-4,6-pregnadiene-3,20-dione comprising ketalizing the 20-keto group of 17α-hydroxy-1,4,6-pregnatriene-3,20-dione with ethylene glycol in the presence of a trialkyl formate and a strong acid; methylenating the resultant 20-ketal steroid in the 1,2-position by reacting it with trimethylsulfoxonium iodide in a polar aprotic solvent in the presence of a strong base; hydrolyzing the resultant product; and acetylating the resulting 17α-hydroxy-1,2-methylene-4,6-pregnadiene-3,20-dione by reacting it with a reactive derivative of acetic acid in the presence of a strong inorganic or organic sulfonic acid.

2. A process of claim 1, wherein the trialkyl formate is trimethyl or triethyl formate.

3. A process of claim 1, wherein the strong acid in the ketalization is p-toluenesulfonic acid or sulfuric acid in an amount of 0.1–2 mole equivalents based on the keto steroid.

4. A process of claim 1, wherein the polar aprotic solvent is dimethyl sulfoxide, dimethylformamide, dimethylacetamide or hexamethylphosphorotriamide.

5. A process of claim 1, wherein the strong base is NaOH or KOH.

6. A process of claim 1, wherein said strong inorganic or organic sulfonic acid is sulfuric or perchloric acid.

7. 17α-hydroxy-1,4,6-pregnatriene-3-one-20-ethylene ketal.

* * * * *